United States Patent
Ott et al.

(10) Patent No.: US 10,961,182 B2
(45) Date of Patent: Mar. 30, 2021

(54) SOLVENT-FREE ALKANE SULFONATION

(71) Applicant: BASF SE, Ludwigshafen (DE)

(72) Inventors: Timo Ott, Duisburg (DE); Ingo Biertümpel, Duisburg (DE)

(73) Assignee: BASF SE, Ludwigshafen (DE)

( * ) Notice: Subject to any disclaimer, the term of this patent is extended or adjusted under 35 U.S.C. 154(b) by 0 days.

(21) Appl. No.: 16/349,113

(22) PCT Filed: Nov. 27, 2017

(86) PCT No.: PCT/EP2017/080495
§ 371 (c)(1),
(2) Date: May 10, 2019

(87) PCT Pub. No.: WO2018/096138
PCT Pub. Date: May 31, 2018

(65) Prior Publication Data
US 2019/0270701 A1    Sep. 5, 2019

(30) Foreign Application Priority Data
Nov. 28, 2016 (EP) .................................... 16200928

(51) Int. Cl.
| C07C 303/06 | (2006.01) |
| C07C 409/44 | (2006.01) |
| C07C 303/44 | (2006.01) |
| C07C 309/04 | (2006.01) |
| C07C 407/00 | (2006.01) |

(52) U.S. Cl.
CPC .......... *C07C 303/06* (2013.01); *C07C 409/44* (2013.01); *C07C 303/44* (2013.01); *C07C 309/04* (2013.01); *C07C 407/00* (2013.01)

(58) Field of Classification Search
CPC ... C07C 303/06; C07C 303/44; C07C 309/04; C07C 409/44
See application file for complete search history.

(56) References Cited

U.S. PATENT DOCUMENTS

| 2,493,038 A | 1/1950 | Snyder et al. |
| 2,619,507 A | 11/1952 | Jones et al. |
(Continued)

FOREIGN PATENT DOCUMENTS

| CN | 1732141 A | 2/2006 |
| EP | 1558353 B1 | 6/2016 |
(Continued)

OTHER PUBLICATIONS

Mukhopadhyay, S. et al, Direct liquid-phase sulfonation of methane to methanesulfonic acid by SO3 in the presence of metal peroxide, Angew. Chem, Int. Ed, vol. 42, No. 9, pp. 1019-1021 (Year: 2003).*
(Continued)

*Primary Examiner* — Yate' K Cutliff
(74) *Attorney, Agent, or Firm* — Arent Fox LLP

(57) ABSTRACT

The present invention relates to an alkane-sulfonation process using alkane and sulfur trioxide, especially pure sulfur trioxide (100%) under solvent-free conditions in the presence of an initiator. It further relates to the use of a precursor which forms "in-situ" an initiator for manufacturing of alkanesulfonic acids, especially methanesulfonic acids.

9 Claims, 1 Drawing Sheet

(56) References Cited

U.S. PATENT DOCUMENTS

| | | | |
|---|---|---|---|
| 4,680,095 A | | 7/1987 | Wheaton |
| 4,910,335 A | | 3/1990 | Wheaton |
| 5,154,912 A | | 10/1992 | Schirmann et al. |
| 5,304,360 A | * | 4/1994 | Lane .................. B01J 19/2415 423/521 |
| 7,119,226 B2 | | 10/2006 | Sen et al. |
| 7,282,603 B2 | | 10/2007 | Richards |
| 9,902,689 B2 | | 2/2018 | Ott et al. |
| 10,329,251 B2 | | 6/2019 | Ott et al. |
| 2005/0070614 A1 | * | 3/2005 | Richards ............... C07C 303/06 518/700 |
| 2007/0282151 A1 | * | 12/2007 | Richards ............... C07C 303/02 585/733 |
| 2008/0161591 A1 | | 7/2008 | Richards |
| 2016/0289176 A1 | | 10/2016 | Ott et al. |
| 2016/0289181 A1 | | 10/2016 | Ott et al. |

FOREIGN PATENT DOCUMENTS

| | | | | |
|---|---|---|---|---|
| WO | | 2004-041399 A2 | | 5/2004 |
| WO | | 2005-069751 A2 | | 8/2005 |
| WO | | 2007-136425 A2 | | 11/2007 |
| WO | | 2015-071351 A1 | | 5/2015 |
| WO | | 2015-071365 A1 | | 5/2015 |
| WO | | 2015-071371 A1 | | 5/2015 |
| WO | | 2015-071455 A1 | | 5/2015 |
| WO | WO 2015/071455 | | * 5/2015 | ........... C07C 309/00 |

OTHER PUBLICATIONS

Haskins, "The Application of Stable Isotopes in Biomedical Research", Biomedical Mass Spectrometry, 9(7), 269-277.

Korth et al.,; "Direct Spectroscopic Detection of Sulfonyloxyl Radicals And First Measurements Of Their Absolute Reactivities1A", Journal Physics Chemical, 94, 8835-8839 (1990).

Willstätter et al., "On The Knowledge Of Caro's Acid", Chemical Laboratory Of The Schweizerisches Polytechnikum Of Zurich, 27 pages (Apr. 26, 1909).

International Search Report and The Written Opinion of PCT/EP2017/080495, dated Jan. 16, 2018, 7 pages.

Chinese Second Office Action of Application No. 2014800614035, dated Oct. 26, 2017; 16 pages.

Office Action dated Jul. 26, 2017 for U.S. Appl. No. 15/035,865, 19 pages.

Amendment dated Jan. 26, 2018 for U.S. Appl. No. 15/035,865 in response to Office Action dated Jul. 26, 2017, 12 pages.

Office Action dated May 7, 2018 for U.S. Appl. No. 15/035,865, 12 pages.

Amendment dated Aug. 3, 2018 for U.S. Appl. No. 15/035,865 in response to Office Action dated May 7, 2018, 11 pages.

Final Office Action dated Nov. 23, 2018 for U.S. Appl. No. 15/035,865, 22 pages.

Amendment After Final dated Jan. 23, 2019 for U.S. Appl. No. 15/035,865 in response to Final Office Action dated Nov. 23, 2018, 10 pages.

Supplemental Amendment After Final dated Feb. 1, 2019 for U.S. Appl. No. 15/035,865 in response to Final Office Action dated Nov. 23, 2018, 3 pages.

Office Action dated Jan. 24, 2017 for U.S. Appl. No. 15/036,215, 25 pages.

Amendment dated Apr. 21, 2017 for U.S. Appl. No. 15/036,215 in response to Office Action dated Jan. 24, 2017.

371 of PCT/EP2014/074747, filed Nov. 17, 2014, for U.S. Appl. No. 15/035,865, filed May 11, 2016.

371 of PCT/EP2014/074500, filed Nov. 13, 2014, for U.S. Appl. No. 15/036,215, filed May 12, 2016.

International Preliminary Report from the corresponding PCT International Application No. PCT/EP2017/080495 dated Jun. 6, 2019.

* cited by examiner

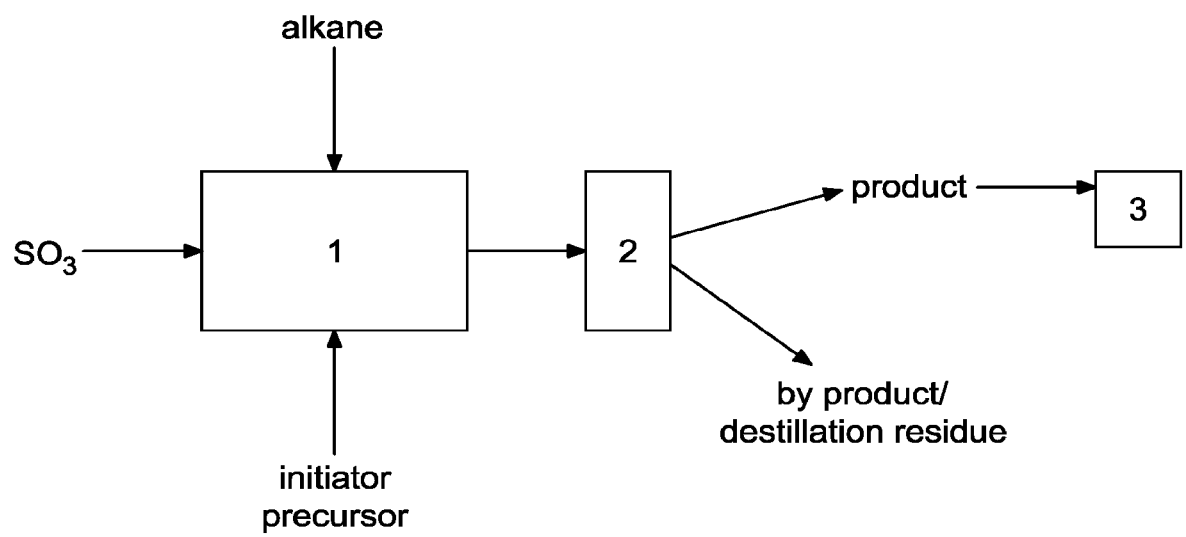

SOLVENT-FREE ALKANE SULFONATION

This application is a National Stage filing of PCT Application No.: PCT/EP2017/080495, filed Nov. 27, 2017, which claims priority to European Patent Application No.: 16200928.6, filed Nov. 28, 2016, both of which are hereby incorporated herein by reference.

TECHNICAL FIELD

The present invention relates to an alkane-sulfonation process using alkane and sulfur trioxide, especially pure sulfur trioxide (100%) under solvent-free conditions in the presence of an initiator. It further relates to the use of a precursor which forms "in-situ" an initiator for manufacturing of alkanesulfonic acids, especially methanesulfonic acids.

BACKGROUND

Alkanesulfonic acids are organic acids that can reach a similar acid strength as that of inorganic mineral acids, for example, sulfuric acid. However, in contrast to usual mineral acids such as sulfuric and nitric acids, the sulfonic acids are non-oxidizing and do not give off vapors that are harmful to health, as can be observed with hydrochloric and nitric acids. Further, many sulfonic acids, for example, methanesulfonic acid, are biologically degradable. The applications of sulfonic acids are many, for example, in cleaning agents, surfactants, galvanic and electronic industry, as catalysts, and in organic synthesis, pharmaceutical chemistry, for example, as protective groups. The salts of sulfonic acids are employed, for example, as surfactants, for example, sodium dodecylsulfonate, or in the electroplating industry, especially as tin, zinc, silver, lead and indium, but also other metal, alkylsulfonates. Furthermore, organic salts are employed in pharmaceutical chemistry. The very high solubility of alkyl sulfonates plays an important role, in particular. Further, no harmful gases are formed in electrolysis, and the use of toxic compounds, for example, cyanide, which is common in many cases, is dispensed with. The structurally simplest representative of alkanesulfonic acids is methanesulfonic acid. U.S. Pat. No. 2,493,038 describes the preparation of methanesulfonic acid from $SO_3$ and methane US 2005/0070614 describes further methods for preparing methanesulfonic acid, and its application. The methods known in the prior art are in part complicated, cost-intensive, and lead to undesirable products because of the harsh reaction conditions.

Introduction and Summary of the Invention

The reaction conditions in conventional processes of alkanesulfonic acid production can result in undesirable side products, which even manifest themselves as disturbing inhibitors in the production of alkanesulfonic acids. This may lead to termination of the actual reaction for preparing the alkanesulfonic acid, but also to impurities, formation of side products and poor yields, based on sulfur trioxide and methane.

WO 2007/136425 A2 discloses the use of the compound di(methanesulfonyl) peroxide (DMSP), which must be prepared by a complex electrolysis and, in addition, is a crystallizable highly explosive solid, as an initiator in a reaction in which methanesulfonic acid is formed from sulfur trioxide and methane.

WO 2015/071365 A1 and WO 2015/071455 A1 both describe processes for the sulfonation of alkanes. The main steps are:
1) Synthesis of an initiator/initiator-solution.
2) Preparation of a sulfur trioxide-solution (oleum) by dissolving sulfur trioxide in an inert solvent (e.g. sulfuric acid)
3) Reaction of oleum with the corresponding alkane after or during addition of the initiator/initiator-solution in a high-pressure-reactor.
4) Quenching of non-reacted starting material
5) Purification (e.g. distillation, crystallization etc.)
6) Recycling of the inert solvent (e.g. sulfuric acid).

BRIEF DESCRIPTION OF THE DRAWINGS

The FIGURE is a scheme of a process for the sulfonation using pure sulfur trioxide of an alkane (e.g. methane) including purification (e.g. distillation) as well as of a device for the production of methanesulfonic acid.

DETAILED DESCRIPTION OF THE INVENTION

It is the object of the present invention to provide an improved process for manufacturing alkanesulfonic acid, especially methanesulfonic acid, allowing improved reaction control. Further, requirements for sulfurtrioxide and alkanes should be not of relevance, meaning that not only absolute pure raw materials might be used, but that impurities do not affect negatively the reaction.

The object of the present invention is achieved by use of a compound of the formula (I)

$$\text{ALK-SO}_2\text{—O—O—X}, \qquad (I)$$

wherein ALK is a branched or unbranched alkyl group, especially a methyl, ethyl, propyl, butyl, isopropyl, isobutyl group, or a higher alkyl group, and X=hydrogen, zinc, aluminium, an alkali or alkaline earth metal, as an initiator-precursor for preparing alkanesulfonic acids, especially methanesulfonic acids from alkane, especially methane, and sulfur trioxide, especially pure sulfur trioxide.

In a further embodiment the object of the invention is achieved by a process for manufacturing the compound as defined above with X=H, comprising reacting an alkanesulfonic acid, especially methanesulfonic acid, with hydrogen peroxide. It might be followed by the isolation of the compound.

In a further embodiment, the object of the invention is achieved by a process for manufacturing alkanesulfonic acids, especially methanesulfonic acid, comprising the following steps:
- providing sulfur trioxide;
- reacting the sulfur trioxide with an alkane, especially methane, in a high-pressure autoclave or laboratory reactor;
- setting a pressure of from 1 to 200 bar;
- preparing the initiator-precursor according to formula (I), by reacting an alkanesulfonic acid or a solution containing the alkanesulfonic acid with a 30% to 100% (w/w) hydrogen peroxide solution;
- adding the initiator-precursor according to formula (I) or a solution thereof to the reactor;
- controlling the temperature of the reaction mixture at 0° C. to 100° C.;
- if necessary purifying the reaction product, for example, by distillation or extraction.

After the reaction has taken part, the reaction mixture contains essentially of the respective alkanesulfonic acid, especially methanesulfonic acid, as well as sulfuric acid. This mixture of alkanesulfonic acid, especially methanesulfonic acid (MSA), and H₂SO₄ might afterwards be used as the respective mixture. The combination of an alkanesulfonic acid, especially methanesulfonic acid, and sulfuric acid provides a strong acid in which even gold might be dissoluted enabling different fields of technical applicability.

Alternatively, the alkanesulfonic acid, especially MSA, might be separated i.e. the method of the invention comprises the optional step of the purifying the reaction product, which might be done by distillation or extraction.

But also alkanesulfonic acids, and specially methanesulfonic acids, might be used in different technical fields, i.e. as cleaning agent (cleaning comprising the area of cleaning and caring, home care as well as industrial and institutional cleaning of hard and soft surfaces, i.e. in dishwashing, commercial laundry, cleaning and sanitation, vehicle and transportation care, concrete cleaning, membrane cleaning, and others), for regeneration of ion exchange resins, in galvanic proceedings, in the area of oil, gas, mining, treatment of metals and/or their surfaces, in different areas of pharmaceutical, chemical and argro-chemical industry or in the production of biodiesel. MSA might also be used in galvanization process of plastics, the broad area of batteries, such as lead battery recycling and recycling in general, such as metal recycling, as well as borane generation are further possible areas of application.

This invention enables major modifications leading to an improved process compared with the prior art by:

Preparing the preferred initiator "in situ" using less or even no solvent.
Easier purification of the product, due to higher product-concentrations
No recycling of the inert solvent.
Where applicable:
Avoiding the preparation of sulfur trioxide-solutions.
Reaction conditions without added solvent.
Evaporating non-reacted sulfur trioxide, instead of quenching.

In particular, the compound as defined above in formula (I) is present in a mixture of the invention which contains additionally at least one compound selected from the group consisting of formula II to XI, i. e. II, III, IV, V, VI, VII, VIII, IX, X, or XI:

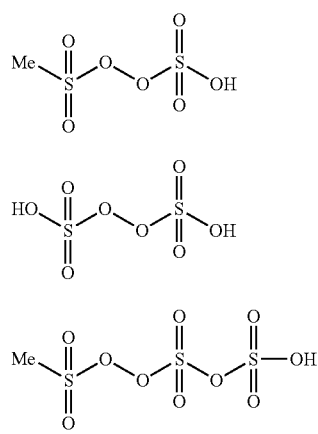

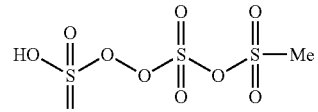

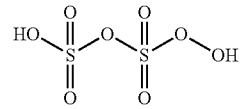

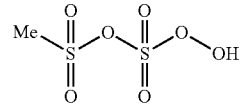

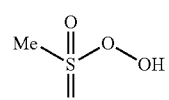

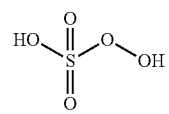

and combinations thereof.

In another embodiment the compound as defined above or the mixture of the invention is present in sulfuric acid or alkanesulfonic acid, especially methanesulfonic acid.

For example, the compound of formula (I) with X=H can be manufactured by a process comprising reacting alkanesulfonic acids, especially methanesulfonic acid, with hydrogen peroxide. The thus obtained compound might be isolated but will preferably be used as initiator-precursor without any further isolation and/or cleaning step.

In particular, the isolation can be effected by extraction, chromatography, precipitation, recrystallization, freeze-drying or similar methods under mild conditions. In a particular embodiment of the process according to the invention, the isolation can be effected by means of precipitation or chromatography. Inert support materials and inert solvents, such as sulfuric or sulfonic acids, are employed therein. The use of organic solvents is also possible.

Inert support materials used for isolation are in particular those which do not negatively interfere with components being the actual reaction partners, e.g. by reducing the yield of the compound of the invention. Furthermore, inert support materials can either chemisorb or physisorb—or both—a chemical compound, without destroying its functionality or structure in an irreversible way. Examples are materials based on e.g. silicon dioxide, aluminium oxide, zirconium oxide and the like.

Surprisingly it has been found that instead of using oleum, as described in the prior art, also pure sulfur trioxide can be used according to the present invention. This avoids the preparation of sulfur trioxide solutions. The reaction conditions are here without added solvents. Further, non-reacted sulfur trioxide can evaporate, avoiding the necessity quenching it.

In a further embodiment, sulfur trioxide is used in a form of oleum with a trioxide content of 50% (w/w) or less, or 65% (w/w) or more. Surprisingly it has been found that contrary to the prior art for the processes of the present invention also oleum with a sulfur trioxide content of 65% (w/w) or more, especially of 70% w/w or more can be used without negatively affecting the inventive process. Even pure sulfur trioxide (100% (w/w) sulfur trioxide) may be used.

Due to the advantages being connected with the use of pure sulfur trioxide mentioned above, the use of pure sulfur trioxide is preferred in the process for manufacturing alkanesulfonic acids according to the present invention. As contrary to the prior art, a circulation of solvent is not necessary, alkanes comprising higher amounts of impurities compared to the prior art can be used. Impurities usually are enriched in the solvent leading to a reduced yield of MSA. By avoiding solvents and thus a circulation of them, impurities originating from the alkanes are not negatively influencing the production of MSA when pure sulfur trioxide is employed.

The invention also relates to a process for manufacturing alkanesulfonic acids especially methanesulfonic acids, comprising the steps stated below:

Sulfur trioxide, especially pure sulfur trioxide is reacted with an alkane in a reactor. For alkanes with a low boiling point, the use of a high-pressure reactor is necessary. For pentane and higher alkanes, a common laboratory reactor is sufficient. In the case of gaseous alkanes, for example, methane, a pressure of 1 to 200 bar gas pressure is set. The initiator-precursor (e.g. alkanesulfonic hydroperoxide) that reacts "in situ" to a suitable initiator is added to this solution. The initiator-precursor is prepared by reacting an alkanesulfonic acid or a solution of such alkanesulfonic acid with hydrogen peroxide to the alkanesulfonic hydroperoxide according to the reaction scheme 1 and can optionally be isolated:

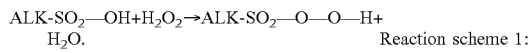

ALK-SO$_2$—OH+H$_2$O$_2$→ALK-SO$_2$—O—O—H+ H$_2$O.    Reaction scheme 1:

The alkanesulfonic hydroperoxide (initiator-precursor) reacts "in situ" during the addition to the reactor to an alkanesulfonic sulfuric peroxoanhydride according to reaction scheme 2:

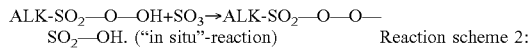

ALK-SO$_2$—O—OH+SO$_3$→ALK-SO$_2$—O—O— SO$_2$—OH. ("in situ"-reaction)    Reaction scheme 2:

Respective alkanesulfonic sulfuric peroxoanhydrides as initiators in the production of methanesulfonic acids are described in WO 2015/071455 A1. In said prior art document, the initiator is produced first in an additional reactor and afterwards added to the main reactor in which the process for the production of methanesulfonic acid or any other alkanesulfonic acid takes place. Contrary thereto, in the present application an initiator precursor is formed which might be isolated but can be added without further purification. Said initiator precursor, being an alkanesulfonic hydroperoxide, reacts in-situ during the addition to the main reactor with the alkane and sulfur trioxide to form methanesulfonic acid.

The concentration of the hydrogen peroxide may be 20 to 100% (w/w). Subsequently, the reaction is completed at 0 to 100° C. The raw product can be processed by extraction, crystallization, distillation or chromatography.

This process can be applied in both batch- and continuous reactor systems.

The invention further relates to the use of an initiator precursor as defined above or a mixture as defined above in a device for performing the process for manufacturing an alkanesulfonic acid, especially methansulfonic acid, wherein the device comprises a reactor (1) in which sulfur trioxide reacts with the compound of formula (I) as initiator-precursor to form an initiator; and reaction of said "in-situ"-built initiator with an alkane, especially methane; a distillation means (2) for distilling the product formed in the reactor (1); and a filling means (3); as well as connection means to connect the reactor (1) with the distillation means (2), and the filling means (3) with the distillation means (2). The FIGURE is a scheme of a process for the sulfonation using pure sulfur trioxide of an alkane (e.g. methane) including purification (e.g. distillation) as well as of a device for the production of methanesulfonic acid.

The process according to the invention allows for alkanesulfonation, especially methanesulfonation, in a reactor system using sulfur trioxide, especially pure sulfur trioxide, with alkane, especially methane, with addition of an initiator precursor. The raw product might be purified by distillation, enabling the production of alkanesulfonic acid in high purity, especially methanesulfonic acid, as distillate.

In the following the invention is further illustrated in an exemplary way taken the preparation of methanesulfonic acid as an example.

Example 1

Preparation of the Initiator-Precursor Solution

To 100 ml of methanesulfonic acid, 78 ml of 60% (w/w) hydrogen peroxide was added dropwise with external cooling and intensive stirring.

Synthesis Protocol:

In a 3.75 L autoclave, 2000 g of pure sulfur trioxide was charged, and the temperature controlled to 50° C. After a pressure of 100 bar of methane gas was set, intensive stirring is performed. Now, the initiator-precursor is metered dropwise to the solution. The pressure dropped down to 50 bar within 30 minutes. Afterwards the pressure was set to 100 bar again. The pressure dropped again down to 50 bar. The pressure was set again to 100 bar. Finally, the pressure dropped down to 30 bar. The yield is higher than 90%, based on sulfur trioxide. The reaction product contains 91% (w/w) methanesulfonic acid.

The invention claimed is:

1. A method of preparing methanesulfonic acid, comprising:
   mixing a compound of the formula (I)

ALK-SO$_2$—O—O—X    (I), wherein ALK is a methyl group, ethyl and X is selected from the group consisting of hydrogen, zinc, aluminum, an alkali metal and an alkaline earth metal, with a first mixture comprising methane, and sulfur trioxide, to form a second mixture comprising the methanesulfonic acid.

2. The method of claim 1, further comprising:
   before the mixing, reacting methanesulfonic acid with hydrogen peroxide to form the compound of formula (I).

3. The method of claim 1, wherein X in formula (I) is H.

4. The method of claim 1, comprising, during the mixing, adding an initiator composition comprising the compound of formula (I) to the first mixture, wherein the initiator composition does not contain SO$_3$.

5. The method of claim 1, wherein during the mixing the compound of formula (I) reacts with SO$_3$ to form a compound of formula (II)

ALK-SO$_2$—O—O—SO$_2$—OX    (II).

6. The method of claim 1, wherein the mixing includes combining an initiation solution comprising the compound of formula (I) and at least one selected from the group consisting of hydrogen peroxide and water, with the first mixture.

7. The method of claim 6, wherein the initiation solution does not contain oleum.

8. The method of claim 1, wherein the mixing is carried out in the absence of sulfuric acid.

9. The method of claim 1, wherein the compound of formula (I) is formed in situ during the mixing.

* * * * *